United States Patent [19]

Gottlieb

[11] 4,061,731

[45] Dec. 6, 1977

[54] COMPOSITIONS CONTAINING COLLAGEN AND METHODS OF USE FOR REPAIRING DEPRESSED CUTANEOUS SCARS

[76] Inventor: Sheldon K. Gottlieb, 8708 Wandering Trail Drive, Potomac, Md. 20854

[21] Appl. No.: 764,229

[22] Filed: Jan. 31, 1977

Related U.S. Application Data

[63] Continuation-in-part of Ser. No. 576,858, June 4, 1975, Pat. No. 4,006,220.

[51] Int. Cl.$^2$ .................... A61K 35/16; A61K 37/02
[52] U.S. Cl. .................................... 424/101; 424/177
[58] Field of Search ................................ 424/101, 177

[56] References Cited

PUBLICATIONS

Kantemirova–Chem. Abst., vol. 84 (1976) p. 2652.

Primary Examiner—Sam Rosen
Attorney, Agent, or Firm—Schwartz & Weinrieb

[57] ABSTRACT

Compositions useful for the repair of depressed cutaneous scars comprising at least one fibrin stabilizer and plasma, if desired, wherein said fibrin stabilizer is present in an amount effective to maintain fibrin within a cavity preferably formed under said scar. One fibrin stabilizer used is finely-divided collagen. The compositions promote the build-up of new collagen within the aforementioned cavity.

18 Claims, No Drawings

COMPOSITIONS CONTAINING COLLAGEN AND METHODS OF USE FOR REPAIRING DEPRESSED CUTANEOUS SCARS

This application is a continuation-in-part of my co-pending application, Ser. No. 576,858, filed June 4, 1975 now U.S. Pat. No. 4,006,220.

BACKGROUND OF THE INVENTION

This invention relates to a method and compositions useful for the repair of depressed cutaneous scars such as those which are characteristic of acne vulgaris. More particularly, this invention relates to the use of at least one fibrin stabilizer in combination with plasma to achieve the desired results of this invention.

In the past, depressed cutaneous scars such as those associated with acne vulgaris have been treated by a number of techniques, the most notable of which is dermabrasion. This procedure is often excessively bloody and usually prolonged. In addition to waiting about two or more weeks for wound sites to heal and to evaluate the degree of sucess, it has been found that this procedure occasionally results in undesired pigmentary changes. Other techniques including such drawbacks include the incising and excising of the skin overlying the scar. Accordingly, a need therefore exists to eliminate these disadvantages and to provide a more effeicient, beneficial and cosmetically acceptable process and composition useful for carrying out said process, for both the doctor and patient.

OBJECTS OF THE INVENTION

It is therefore a significant object of this invention to provide both a method and compositions useful for the repair of depressed cutaneous scars which overcome the disadvantages associated with previously known methods.

Another significant object of this invention is the provision of a new method for repairing depressed cutaneous scars which eliminates the need for surgical incisions or excisions.

A still further object of this invention is a method and composition capable of permanently repairing amenable depressed ovoid and linear lesions with immediate beneficial and cosmetically acceptable results without having to incise, excise or abrade the skin overlying the scar.

Still another object of this invention is the provision of a simple and efficient process and composition capable of enhancing tissue healing in a shorter period of time by the stabilization of fibrin which regulates connective tissue formation.

The invention will be better understood and objects other than those set forth above will become apparent after reading the following detailed description of preferred, yet illustrative, embodiments hereof.

BRIEF SUMMARY OF THE INVENTION

Briefly, the present invention relates to a composition useful for the repair of depressed cutaneous scars comprising at least one fibrin stabilizer and plasma wherein at least one of said fibrin stabilizers is finely divided collagen. Another embodiment of this invention relates to a method for repairing depressed cutaneous scars comprising the step of introducing at least one fibrin stabilizer and plasma intradermally beneath a depressed scar. According to this method when only one fibrin stabilizer is used, said stabilizer is finely divided collagen. If more than one stabilizer is used in the process, then at least one of said stabilizers must be finely divided collagen.

In addition to finely divided collagen, other fibrin stabilizers used in the practice of this invention can be any of the well known agents useful for promoting the build-up of fibrin in a given region. One such material is absorbable gelatin sponge which is a sterile, substantially water-insoluble, non-antigenic, completely proteolytically digestable pulverized gelatin sponge. A process for preparing absorbable gelatin sponge is disclosed in U.S. Pat. No. 2,464,357. This particular fibrin stabilizer functions as a stabilizer by trapping fibrin and fibrin precursors when introduced intradermally beneath a depressed scar thereby significantly enhancing the build-up of new collagen tissue beneath said scar. In addition, this stabilizer also traps fibroblasts which replace fibrin to build the desired tissue up to the normal level.

Another useful fibrin stabilizer are those agents capable of inhibiting plasminogen activators which are responsible for the dissolution of newly formed fibrin and include aminocaproic acid (6-aminohexanoic acid) of the formula $NH_2CH_2(CH_2)_4COOH$ and aminocaproic acid compounds of the formula:

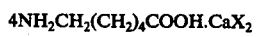

$$4NH_2CH_2(CH_2)_4COOH \cdot CaX_2$$

wherein X is halogen and preferably chloride or bromide, and other similar functioning compounds. Aminocaproic acid is prepared in accordance with Japenese Pat. Nos. 215,676 and 215,679.

The fibrin stabilizer employed in the compositions of this invention is finely divided collagen, said collagen preferably being a finely divided fibrous mass consisting of essentially collagen or an ionizable partial salt of collagen. Acids used to form the partial salts include, e.g., hydrochloric acid, sulfuric acid, hydrobromic acid, phosphoric acid, cyanoacetic acid, acetic acid, citric acid and lactic acid. Best results are believed to be achieved when at least 85 percent of the fibers have a length of less than 1 mm. Processes for preparing said finely divided collagen useful for the practice of this invention are disclosed in U.S. Pat. Nos. 3,628,974 and 3,742,955, said processes being incorporated herein by reference. Finely divided collagen is believed to function in a manner similar to the finely divided absorbable gelatin sponge discussed hereinbefore.

According to a preferred embodiment of this invention, the finely divided collagen is employed with absorbable gelatin sponge and/or aminocaproic acid (and structurally related compounds thereof) although it is understood that each of said agents can be used individually or in combination with human blood plasma.

The fibrin stabilizer used is preferably employed in combination with plasma which is preferably of human origin and preferably from the same patient being treated in accordance with this invention. The plasma can be initially admixed with at least one fibrin stabilizer, or the blood containing plasma can be permitted to flow into the cavity produced by the preliminary step of transecting the scar tissue under the scar and the accompanying injury to said tissue thereby forming said cavity.

The amount of fibrin stabilizer used in combination with plasma and introduced into said cavity is dependent upon the particular fibrin stabilizer(s) employed and the size of the cavity formed beneath the depressed cutaneous scars by the transecting step, but in any event is an amount sufficient to maintain a minimum amount of fibrin within said cavity thereby resulting in the build-up of new collagen within said cavity thereby resulting in the permanent elevation of the depression to a more cosmetically acceptable level thereby producing a substantially more continuous skin surface that improves the cosmetic appearance of the patient.

Generally, the amount of finely divided collagen employed in the practice of this invention is between about 5 and 50 mg., and preferably between about 20 and 30 mg. for up to 0.5 cc of plasma introduced into the cavity. The compositions of this invention contain from about 0 to 50 mg., generally between about 5 to 50 mg. or 20 to 50 mg. and preferably between about 30 and 40 mg. of proteolytically digestable pulverized absorbable gelatin sponge. In addition, the compositions contain from about 0 to 75 mg., generally between about 12.5 to 75 mg. and preferably between about 30 and 40 mg. of aminocaproic acid or the aminocaproic acid compounds as defined hereinbefore. The amounts set forth herein for both said sponge and aminocaproic acid are for each 0 to 0.5 cc. and preferably 0.3 to 0.5 cc. of plasma introduced into said cavity. It is understood that water or saline solution may be substituted in whole or in part on a volume for volume basis.

Best results are believed to be achieved when a mixture consisting of: (1) from about 5 to 50 mg. of finely divided collagen, (2) from about 0 to 50 mg. of pulverized absorbable gelatin sponge, and (3) from about 0 to 75 mg. of aminocaproic acid is used for each 0 to 0.5 cc. and preferably between 0.3 and 0.5 cc. of plasma introduced into said cavity.

It is understood that the finely divided collagen, preferably finely divided fibrous collagen as defined hereinbefore, can be added directly beneath the depressed cutaneous scar without having pulverized absorbable gelatin sponge and/or aminocaproic acid admixed therewith. When finely divided collagen is administered in this manner, from 5 to 50 mg. of said finely divided collagen is admixed with from about 0.3 to 0.5 cc. of saline solution or water or other pharmaceutically acceptable inert carrier.

When a cavity is formed beneath depressed cutaneous scars, it is understood that most cavities formed are by means of a transecting step resulting in the formation of a cavity having a diameter of between about 3 and 5 millimeters. In achieving the desired results of this invention, usually between about 0.3 and 0.5 cc of plasma are introduced into a cavity having the aforementioned dimensions with a proportionally greater amount of plasma being introduced into a larger cavity.

It is further understood that the source of plasma, if introduced, is preferably from either a sample of blood originally obtained from the patient or from the blood plasma flowing into the cavity immediately after the formation thereof or from a combination of the two sources. It is the plasma fibrinogen and the thrombin located in the cavity of the injured tissue that reacts and ultimately results in the formation of fibrin which is replaced by fibroblasts that is required for the build-up of the new tissue resulting in the permanent elevation of the depression to the normal level.

When plasma is used from a blood sample already removed from the patient, it is desirable to obtain said plasma by taking 15 cc of the patient's venous blood and mixing the same with 2.3 cc of anticoagulant citrate dextrose and thereafter centrifuging at 2000 revolutions per minute for 2 minutes. The clear plasma is then collected in a sterile test tube for its subsequent use.

Plasma obtained in this manner or by other conventional procedures, may be either used immediately in the practice of this invention or may be stored for future used, such as in a refrigerator, with conventional additives optionally being incorporated into said plasma to aid in the preservation thereof, which need not be removed for the subsequent use of the plasma in the practice of this invention.

What is claimed is:

1. A composition useful for the repair of depressed cutaneous scars comprising finely-divided collagen and plasma, said collagen being present in an amount effective to maintain fibrin within a cavity formed under said scar and thereby cause the build-up of new collagen within said cavity and said plasma being present in an amount to provide sufficient fibrin within said cavity.

2. The composition of claim 1 wherein said composition contains up to 0.5 cc of human plasma.

3. The composition of claim 2 further comprising at least one additional fibrin stabilizer, said fibrin stabilizer being selected from the group consisting of: (1) pulverized absorbable gelatin sponge, (2) aminocaproic acid, (3) a compound of the formula $4NH_2CH_2(CH_2)_4COOH \cdot CaX_2$ wherein X is chloride or bromide, and (4) mixtures thereof.

4. The composition of claim 3 containing from about 5 to 50 mg. of said pulverized absorbable gelatin sponge for each 0.3 to 0.5 cc of plasma 5. The composition of claim 3 containing from about 12.5 to 75 mg. of aminocaproic acid for each 0.3 to 0.5 cc. of plasma.

6. The composition of claim 3 containing a mixture of said pulverized absorbable gelatin sponge and aminocaproic acid wherein said mixture consists of from 20 to 50 mg. of pulverized absorbable gelatin sponge and from 12.5 to 75 mg. of aminocaproic acid for up to 0.5 cc of plasma.

7. In a method for repairing a depressed cutaneous scar comprising the step of introducing the composition of claim 1 intradermally beneath said scar.

8. The method of claim 7 comprising initially transecting the fibrous tissue beneath said scar thereby forming a cavity.

9. The method of claim 8 comprising introducing a sufficient amount of said composition to stimulate the formation of new tissue thereby resulting in the permanent elevation of the depression to the normal skin level.

10. A composition useful for the repair of depressed cutaneous scars comprising finely-divided collagen in combination with:
   a. pulverized absorbable sponge, or
   b. a member selected from the group consisting of aminocaproic acid, compounds of the formula: $4NH_2CH_2(CH_2)_4COOH \cdot CaX_2$ and mixtures thereof, or
   c. mixtures of (a) and (b),
   wherein the total amount of collagen and components (a) and (b) are present in an amount sufficient to maintain fibrin within a cavity formed under said scar and thereby cause the build-up of new collagen within said cavity.

11. The composition of claim 10 wherein (b) is aminocaproic acid.

12. The composition of claim 11 containing from about 20 to 50 mg. of finely-divided fibrous collagen, 0 to 50 mg. of pulverized absorbable sponge, and 0 to 75 mg. of (b).

13. The composition of claim 12 wherein (b) is present in an amount between 12.5 and 75 mg.

14. In a method for repairing a depressed cutaneous scar comprising the step of introducing the composition of claim 10 intradermally beneath said scar.

15. The method of claim 14 comprising initially transecting the fibrous tissue beneath said scar thereby forming a cavity.

16. The method of claim 15 comprising introducing a sufficient amount of said composition to stimulate the formation of new tissue thereby resulting in the permanent elevation of the depression to the normal skin level.

17. The method of claim 16 wherein said composition further comprises a pharmaceutically acceptable inert carrier.

18. The method of claim 17 wherein said inert carrier is water.

* * * * *